(12) United States Patent
Pavliv

(10) Patent No.: US 11,571,412 B2
(45) Date of Patent: *Feb. 7, 2023

(54) THROMBOXANE RECEPTOR ANTAGONISTS IN AERD/ASTHMA

(71) Applicant: Cumberland Pharmaceuticals Inc., Nashville, TN (US)

(72) Inventor: Leo Pavliv, Cary, NC (US)

(73) Assignee: Cumberland Pharmaceuticals Inc., Nashville, TN (US)

( * ) Notice: Subject to any disclaimer, the term of this patent is extended or adjusted under 35 U.S.C. 154(b) by 25 days.

This patent is subject to a terminal disclaimer.

(21) Appl. No.: 16/687,151

(22) Filed: Nov. 18, 2019

(65) Prior Publication Data

US 2020/0155513 A1 May 21, 2020

Related U.S. Application Data

(63) Continuation of application No. 15/195,265, filed on Jun. 28, 2016, now abandoned.

(60) Provisional application No. 62/186,644, filed on Jun. 30, 2015.

(51) Int. Cl.
*A61K 31/422* (2006.01)
*A61P 11/00* (2006.01)
*A61P 11/06* (2006.01)
*A61K 31/616* (2006.01)

(52) U.S. Cl.
CPC .......... *A61K 31/422* (2013.01); *A61K 31/616* (2013.01); *A61P 11/00* (2018.01); *A61P 11/06* (2018.01)

(58) Field of Classification Search
CPC ..... A61K 31/422; A61K 31/616; A61P 11/00; A61P 11/06
See application file for complete search history.

(56) References Cited

U.S. PATENT DOCUMENTS

| | | |
|---|---|---|
| 4,258,058 A | 3/1981 | Witte et al. |
| 4,416,896 A | 11/1983 | Nakane et al. |
| 4,443,477 A | 4/1984 | Witte et al. |
| 4,537,981 A | 8/1985 | Snitman et al. |
| 4,663,336 A | 5/1987 | Nakane et al. |
| 4,752,616 A | 6/1988 | Hall et al. |
| 4,839,384 A | 6/1989 | Ogletree |
| 4,977,174 A | 12/1990 | Stein et al. |
| 5,066,480 A | 11/1991 | Ogletree et al. |
| 5,100,889 A | 3/1992 | Misra et al. |
| 5,128,359 A | 7/1992 | Bru-Magniez et al. |
| 5,312,818 A | 5/1994 | Rubin et al. |
| 5,399,725 A | 3/1995 | Poss et al. |
| 5,506,248 A | 4/1996 | Nikfar et al. |
| 6,509,348 B1 | 1/2003 | Ogletree |
| 7,785,891 B2 | 8/2010 | Phillips et al. |
| 8,299,097 B2 | 10/2012 | Boyce |
| 9,693,998 B2 | 7/2017 | Pavliv et al. |
| 2003/0040534 A1 | 2/2003 | Hughes et al. |
| 2006/0009496 A1 | 1/2006 | Oates et al. |
| 2009/0012115 A1* | 1/2009 | Phillips ................ A61K 31/405 514/301 |
| 2009/0012136 A1* | 1/2009 | Stephens ................ A61K 45/06 514/374 |
| 2009/0022729 A1 | 1/2009 | Mackman et al. |
| 2013/0197044 A1 | 8/2013 | Pavliv et al. |
| 2014/0275061 A1 | 9/2014 | Orwat et al. |
| 2015/0253327 A1* | 9/2015 | Laidlaw ................ A61K 31/616 514/165 |
| 2017/0258771 A1 | 9/2017 | Pavliv et al. |
| 2017/0312255 A1 | 11/2017 | Pavliv et al. |
| 2017/0319554 A1 | 11/2017 | Pavliv et al. |
| 2017/0340614 A1 | 11/2017 | Pavliv et al. |
| 2018/0050020 A1 | 2/2018 | Pavliv |

FOREIGN PATENT DOCUMENTS

| | | |
|---|---|---|
| EP | 0638310 A1 | 2/1995 |
| JP | H02273625 A | 11/1990 |
| JP | 2008543748 A | 12/2008 |
| WO | 2006132460 A1 | 12/2006 |
| WO | 2008137793 A1 | 11/2008 |
| WO | 2012009545 A1 | 1/2012 |

OTHER PUBLICATIONS

Cumberland Pharmaceuticals; "Study NCT02216357: Trial to Determine the Safety of Oral Ifetroban in Patients With a History of Aspirin Exacerbated Respiratory Disease"; ClinicalTrials.gov archive; Version 1; Aug. 12, 2014 (Year: 2014).*
Lee; "Aspirin-Exacerbated Respiratory Disease: Evaluation and Management"; 2011; Allergy Asthma Immunol. Res; 3(1): 3-10; doi: 10.4168/aair.2011.3.1.3 (Year: 2011).*
Acquaviva, A., et al., "Signaling pathways involved in isoprostane-mediated fibrogenic effects in rat hepatic stellate cells" Free Radical Biology and Medicine, vol. 65, pp. 201-207, Jun. 20, 2013.
Amrstrong, R. et al., Competitive antagonism at thromboxane receptors in human platelets, Brit. J. Pharmacol. 84 (3):595-607, (Mar. 1985).
Angeli, P., et al. "Reversal of type 1 hepatorenal syndrome with the administration of midodrine and octreotide." Hepatology. Jun. 1999;29(6):1690-7.
Armour CL, Johnson PR, Alfredson ML, Black JL. Characterization of contractile prostanoid receptors on human airway smooth muscle. Eur J Pharmacol, 165(2-3):215-22 (1989).
Bianchetti, A. et al., Pharmacological Actions of Levallorphan Allyl Bromide (CM 32191), A New Peripheral Narcotic Antagonist, Life Sci. 31, pp. 2261-2264, (Nov. 15, 1982).

(Continued)

*Primary Examiner* — Timothy P Thomas
(74) *Attorney, Agent, or Firm* — Vivicar Law, PLLC

(57) ABSTRACT

The present invention is directed to methods of treating AERD (aspirin exacerbated respiratory disease) and/or asthma via the administration of a thromboxane receptor antagonist to a patient in need thereof.

4 Claims, 1 Drawing Sheet

(56) References Cited

OTHER PUBLICATIONS

Bochenek G, et al., "A controlled study of 9 alpha, 11 beta PGF2 (a prostaglandin D2 metabolite) in plasma and urine of patients with bronchial asthma and healthy controls after aspirin challenge," J Allergy Clin Immunol, 111(4):743-9 (2003).
Borgdorff, MA et al., "Sildenafil treatment in established right ventricular dysfunction improves diastolic function and attenuates interstitial fibrosis independent from afterload" Am J Physiol Heart Circ Physiol 307, pp. H361-H369. May 30, 2014.
Bresnahan, B., et al. "Mesangial Cell Immune Injury" J. Amer. Society of Nephrology, 1991, pp. 1041-1047.
Brittain, R.T. et al., "AH 23848: A Thromboxane Receptor-Blocking drug that can Clarify the Pathophysiologic Role of Thromboxane A2," Circulation 72(6):1208-1218 (Dec. 1985).
Bruggeman, L.A., et al. "Thromboxane stimulates synthesis of extracellular matrix proteins in vitro" Am. J. Physiol. 261, F488-F494, 1991.
Byland, E. et al., "ICI 185282: A Selective, Potent Thromboxane A2 Receptor Antagonist on Smooth Muscle," Brit. J. Pharmacol. 90 (Proc. Suppl):228 P-Abs, (Mar. 1985).
Castro, Placebo versus Best-Available-Therapy Control Group in Clinical Trials for Pharmacologic Therapies. Proceedings of the AmericanThoracic Society, 570-573 (2007).
Cediel, E., et al. "AT-1 receptor antagonism modifies the mediation of endothelin-1, thromboxane A2, and catecholamines in the renal constrictor response to angiotensin II," Kidney International (2005) 67, pp. 1-10.
Cediel, et al., AT-1 receptor antagonism modifies the mediation of endothelin-1, thromboxane A2, and catecholamines in the renal constrictor response to angiotensin II, 2005, Kidney International, vol. 67, pp. S3-S9.
Clinical Trials.gov; "Trial to Determine the Safety of Oral Ifetroban in Patients With a History of Aspirin Exacerbated Respiratory Disease"; First Posted: Aug. 13, 2014; ClinicaiTrials.gov Identifier: NCT02216357; https://clinicaltrials.gov/ct2/show/NCT02216357; accessed Jan. 12, 2017.
Comporti, M. et al. "F2-isoprostanes stimulate collagen synthesis in activated hepatic stellate cells: a link with liver fibrosis?" Laboratory Investigation, vol. 85, pp. 1381-1391, Aug. 22, 2005.
Liu, T., et al. "Prostaglandin E2 deficiency causes a phenotype of aspirin sensitivity that depends on platelets and cysteinyl leukotrienes" PNAS, Early Edition, pnas.org/cgi/doi/10.1073/pnas.1313185110 , Sep. 9, 2013.
Dockens, R., et al, "Disposition of Radiolabeled Ifetroban in Rats, Dogs, Monkeys, and Humans," Drug Metabolism and Disposition, 2000, vol. 28 No. 8; pp. 973-980.
Dogne, J-M., et al., "Recent developments of thromboxane modulators," Exp. Opin. Ther. Patents 11: 1663-1675 (2001).
Donovan, JP., et al. "Cerebral edema and increased intracranial pressure in chronic liver disease." Lancet. Mar. 7, 1998;351(9104):719-21.
Dr. G. Wright, "Hepatic Encephalopathy; The role of Inflammation, Ammonia and Aquaporin Expression in the Pathogenesis of Cerebral Oedema," Liver failure group, The Institute of Hepatology, University College London, Sep. 2009, pp. 1-292.
Fanelli, F., et al. "Management of refractory hepatic encephalopathy after insertion of TIPS: long-term results of shunt reduction with hourglass-shaped balloon-expandable stent-graft." Am J Roentgenol. Dec. 2009;193(6):1696-702.
Fevery J, et al., "Reversal of hepatorenal syndrome in four patients by peroral misoprostol (prostaglandin E1 analogue) and albumin administration," J Hepatol. 11(2):153-8 (1990).
Fischer AR, et al., "Direct evidence for a role of the mast cell in the nasal response to aspirin in aspirin-sensitive asthma," J Allergy Clin Immunol, 94(6 Pt 1):1046-56 (1994).
Ford-Hutchinson, A.W., et al. "The pharmacology of L-670,596," Can. J. Physiol. Pharmacol., 1989, 67:989-993.

Gardi, C. et al. "F2-isoprotane receptors on hepatic stellate cells" Laboratory Investigation, vol. 88, pp. 124-131 (2007).
Gelosa, P., et al. "Terutroban, a thromboxane/prostaglandin endoperoxide receptor antagonist, prevents hypertensive vascular hypertrophy and fibrosis" Am J Physiol Heart Circ Physiol 300: pp. H762-H768, Dec. 10, 2010.
Gentilini, P., et al. "Renal effects of a thromboxane (TX) A2 receptor antagonist (ONO-3708) in cirrhotics with ascites (C)," Journal of Hepatology, vol. 11, Jan. 1, 1990, p. S25.
Gluud, L.L., et al. "Systematic review of randomized trials on vasoconstrictor drugs for hepatorenal syndrome." Hepatology. 2010 51:576-584.
Grandi, AM et al., "Aldosterone Antagonist Improves Diastolic Function in Essential Hypertension" Hypertension 40, pp. 647-652, 2002.
Guevara M, et al. "Hepatorenal syndrome," Dig Dis. 2005;23(1):47-55.
Guevara M., et al., "Hepatorenal syndrome." Int J Biochem Cell Biol. Jan. 2005;37(1):22-6.
Hall, R.A. et al, "Pharmacology of L-655,240 (3-[1-(4-chlorobenzyl)-5-fluoro-3-methyl-indol-2-yl] 2,2-dimethylpropanoic acid); a potent, selective thromboxane / prostaglandin endoperoxide antagonist," Eur. J. Pharmacol. 135(2):193-201 (Mar. 17, 1987).
Hope et al., "Rational approach to aspirin dosing during oral challenges and desensitization of patients with aspirin-exacerbated respiratory disease," J Allergy Clin Immunol. 123(2):406-10 (2009).
International Search Report, dated Sep. 15, 2016, issued in connection with International Application No. PCT/US2016/039816.
International Search Report in International Application No. PCT/US15/31395, dated Aug. 10, 2015.
Jessup, C.L. et al., "ICI 159995: A Novel Thromboxane A2 Receptor Antagonist," Brit. J. Pharmacol. 86 (Proc. Suppl):808 P-Abs., (Dec. 1985).
Jiang, Q et al., "Cardiovascular Phamtacology Inhibitory effect of ginsenoside Rb1 on calcineurin signal pathway in cardiomyocyte hypertrophy induced by prostaglandin F2alpha" Acta Pharmacologica Sinica 28, p. 1149-1154, 2007.
Kramer, H.J., et al, "Effect of Thromboxane A2 Receptor Blockade on Oliguric Ischemic Acute Renal Failure in Conscious Rats," J. Am. Soc. Nephrol., 1993 vol. 4 No. 1, pp. 50-57.
Kunapuli, P. et al. "Prostaglandin F2alpha (PGF2alpha) and the Isoprostane, 8, 12-iso-Isoprostane F2alpha-III, Induce Cardiomyocyte Hypertrophy" The Journal of Biological Chemistry, vol. 273, No. 35, pp. 22442-22452, May 27, 1998.
Kurokawa, S., et al. "Effect of inhaled KP-496, a novel dual antagonist of the cysteinyl leukotriene and thromboxane A2 receptors, on a bleomycin-induced pulmonary fibrosis model in mice" Pulmonary Pharmacology & Therapeutics, vol. 23, pp. 425-431, 2010.
Laidlaw ™, et al. "Cysteinyl leukotriene overproduction in aspirin-exacerbated respiratory disease is driven by platelet adherent leukocytes," Blood, 119(16):3790-8 (2012).
Lenz K, et al. "Beneficial effect of 8-ornithin vasopressin on renal dysfunction in decompensated cirrhosis," Gut. Jan. 1989;30(1):90-6.
Lenz K, et al. "Ornipressin in the treatment of functional renal failure in decompensated liver cirrhosis. Effects on renal hemodynamics and atrial natriuretic factor," Gastroenterology. Oct. 1991;101(4):1060-7.
Lenz K, et al., "Enhancement of renal function with ornipressin in a patient with decompensated cirrhosis," Gut, 1985;26(12):1385-6.
Liu T, et al., "Prostaglandin E2 deficiency uncovers a dominant role for thromboxane A2 in house dust mite-induced allergic pulmonary inflammation," Proc Natl Acad Sci USA, 109(31):12692-7 (2012).
Liu, T, et al. "Prostaglandin E2 deficiency causes a phenotype of aspirin sensitivity that depends on platelets and cysteinyl leukotrienes" Proc Natl Acad Sci USA. Oct. 15, 2013. Abstract only.
Cumberland Pharmaceuticals, "Cumberland Pharmaceuticals Announces Pipeline Expansion With Boxaban(TM) (ifetroban) Oral Capsule" (2015).
Laidlaw, T. et al., "Platelets in patients with aspirin-exacerbated respiratory disease," J. Allergy and Clinical Immunology, 135(6):1407-1414 (2015).

(56) References Cited

OTHER PUBLICATIONS

Lee, et al. "Aspirin-Exacerbated Respiratory Disease: Evaluation and Management," Allergy Asthma Immunol. Res, 3(1): 3-10 (2011).

Murakami M, et al., Regulation of prostaglandin E2 biosynthesis by inducible membrane-associated prostaglandin E2 synthase that acts in concert with cyclooxygenase-2. J Biol Chem, 275(42):32783-92 (2000).

Nanji, A. et al. "Thromboxane Inhibitors Attenuate Inflammatory and Fibrotic Changes in Rat Liver Despite Continued Ethanol Administrtions" Alcoholism: Clinical and Experimental Research, vol. 37, No. 1, pp. 31-39, Jan. 2013.

Nanji, A. et al. "Thromboxane Inhibitors Attenuate Pathological Changes in Alcoholic Liver Disease in the Rat" Gastroenterology, vol. 112, pp. 200-207, 1997.

Narisada, M et al., S-1452, Shionogi domitroban, Anboxan®. pp. 1-14 (2004).

Ogletree ML, et al., "Interspecies differences in thromboxane receptors: studies with thromboxane receptor antagonists in rat and guinea pig smooth muscles," J Pharmacol ExpTher., 260(2):789-94 (1992).

Peters, et al., "Acute hepatic failure: limitations of medical treatment and indications for liver transplantation." The Clinical Investigator, 1993, vol. 71, No. 11, pp. 875-881.

Pettipher R, et al., "Antagonism of the prostaglandin D2 receptors DP1 and CRTH2 as an approach to treat allergic diseases," Nat Rev Drug Discov, 6(4):313-25 (2007).

Picado C, et al., "Cyclooxygenase-2 mRNA is downexpressed in nasal polyps from aspirin-sensitive asthmatics," Am J Respir Crit Care Med, 160(1):291-6 (1999).

Rosado, E. et al, "Terutroban, a TP-Receptor Antagonist, Reduces Portal Pressure in Cirrhotic Rats" Hepatology, Official Journal of the American Association for the Study of Liver Diseases, pp. 1-12, 2013.

Rosenfeld, L., et al, "Ifetroban Sodium: An Effective TxA2/PGH2 Receptor Antagonist," Cardiovascular Drug Reviews, vol. 19, No. 2, pp. 97-115, 2001.

Sladek K, et al., "Eicosanoids in bronchoalveolar lavage fluid of aspirin-intolerant patients with asthma after aspirin challenge," Am J Respir Crit Care Med, 149(4 Pt 1):940-6 (1994).

Soper CP, et al., "Amelioration of hepatorenal syndrome with selective endothelin-A antagonist," Lancet. Jun. 29, 1996;347(9018):1842-3.

Sousa A, et al., "Enhanced expression of cyclo-oxygenase isoenzyme 2 (COX-2) in asthmatic airways and its cellular distribution in aspirin-sensitive asthma," Thorax, 52(11):940-5 (1997).

Szczeklik A, et al., "Bronchial aspirin challenge causes specific eicosanoid response in aspirin-sensitive asthmatics," Am J Respir Crit Care Med, 154(6 Pt 1):1608-14 (1996).

Wasserman, et al. SKF 88046, Smith Kline & West Laboratories, Pharmacologist 25(3):116 Abs., 117 Abs, (Aug. 1983).

White et al., "Effect of leukotriene modifier drugs on the safety of oral aspirin challenges," Ann Allergy Asthma Immunol., 97(5):688-93 (2006).

Yoshimura T, et al., "Correlation between the prostaglandin D(2)/E(2) ratio in nasal polyps and the recalcitrant pathophysiology of chronic rhinosinusitis associated with bronchial asthma," Allergol Int, 57(4):429-36 (2008).

Adis Insight, "Drug Profile: Ifetroban—Cumberland Pharmaceuticals," available at https://adisinsight.springer.com/drugs/800001981 (retrieved on Sep. 10, 2018).

ClinicalTrials.gov, "Trends, Charts, and Maps," available at https://clinicaltrials.gov/ct2/resources/trends (retrieved on Jul. 17, 2018).

Husted, S. "New developments in oral antiplatelet therapy," European Heart Journal Supplements, 9 (Supplement D): D20-D27 (2007).

* cited by examiner

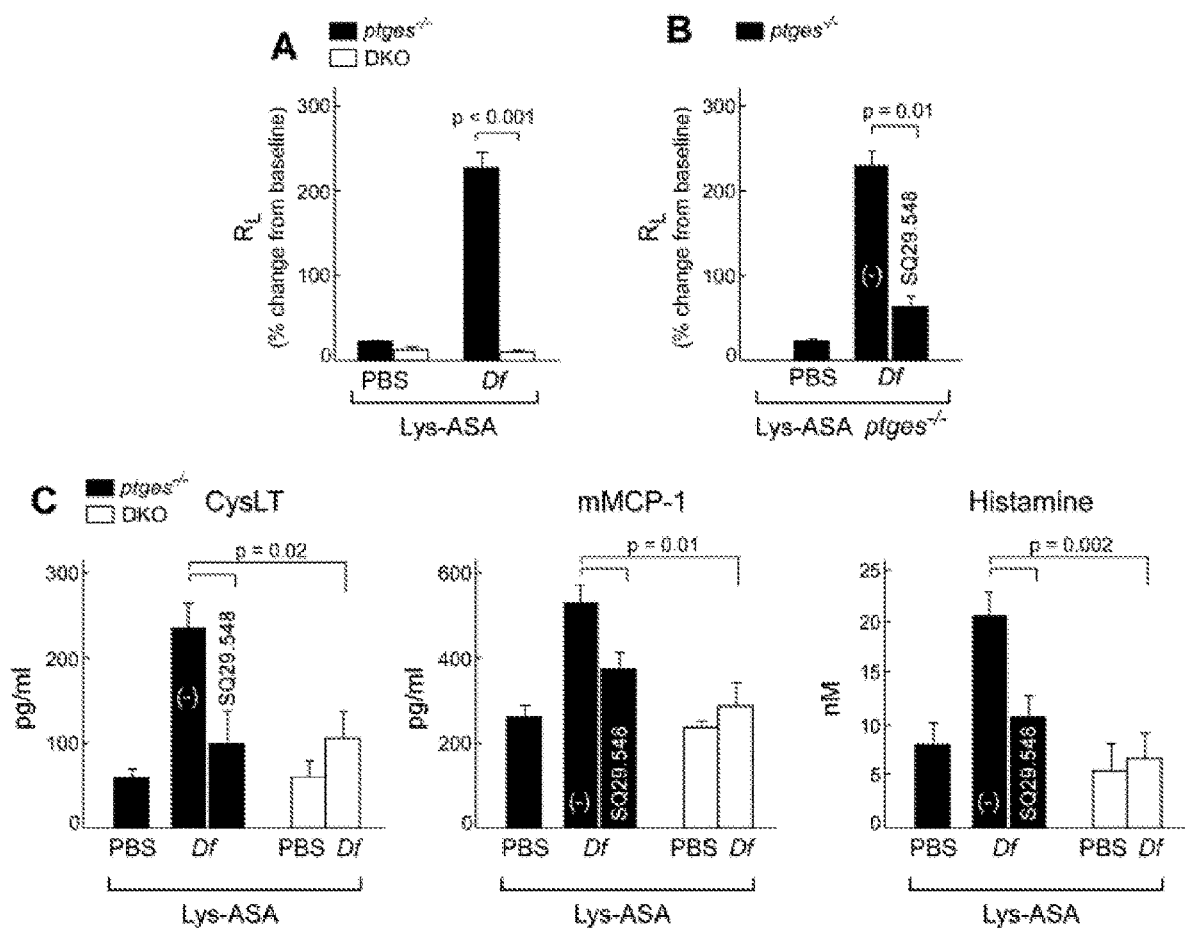

THROMBOXANE RECEPTOR ANTAGONISTS IN AERD/ASTHMA

FIELD OF THE INVENTION

The present invention is related to the use of thromboxane receptor antagonists (e.g., Ifetroban) in the treatment of AERD (aspirin exacerbated respiratory disease) and asthma; and pharmaceutical compositions for the treatment of the same.

BACKGROUND OF THE INVENTION

Aspirin Exacerbated Respiratory Disease (AERD) is a chronic medical condition that consists of asthma, recurrent sinus disease with nasal polyps, as well as a sensitivity to aspirin and other non-steroidal anti-inflammatory drugs (NSAIDs). Patients suffering from typically develop reactions triggered by aspirin or other NSAIDs. These reactions include, but are not limited to increased nasal congestion or stuffiness; eye watering or redness; cough, wheezing, or chest tightness; frontal headache or sensation of sinus pain; flushing and/or a rash; nausea and/or abdominal cramping; and a general feeling of malaise, sometimes accompanied by dizziness.

From a scientific perspective, AERD is characterized by mast cell activation with overproduction of cysteinyl leukotrienes following inhibition of COX-1 by medications like aspirin or NSAIDs. The cause of the mast cell activation that occurs following COX-1 inhibition is unknown.

AERD affects about 10% of adults who have asthma. A large proportion (about 40%) of patients who have asthma and nasal polyps are sensitive to aspirin and NSAIDs.

It is typical that human patients who are suffering from AERD also have asthma, nasal congestion, and nasal polyps. Such patients often do not respond to conventional treatments.

AERD is also commonly referred to as Samter's Triad or Aspirin Sensitive Asthma.

The most common treatment currently available for AERD is aspirin desensitization. Aspirin desensitization may be accomplished, for example, by hospitalizing the patient and instituting a regimen wherein the patient is initially given a very low dose (20-40 mg) of aspirin, with gradual higher doses given every 1.5-3 hours. Following an aspirin-induced reaction (and subsequent stabilization of the patient), further doses of aspirin are administered. The desensitization is considered to be complete once the patient has received a 325 mg dose of aspirin without further reaction. The patient is then discharged and continues treatment with aspirin (typically either 325 mg or 650 mg twice daily). However, aspirin desensitization does not help many AERD patients.

Other treatments include an antibiotic such as tobramycin or biaxin, a salicylate-free diet, a corticosteroid such as betamethasone, and/or acetylcysteine.

Aspirin challenge of subjects with aspirin exacerbated respiratory disease (AERD) results in the activation of mast cells (MCs), as evidenced by increases in the levels of tryptase in both serum (Bochenek 2003) and nasal lavage fluid (Fischer 1994). In addition, the levels of 9α-11β-PGF2, a PGD2 metabolite, increase in the plasma during the reaction to aspirin (Bochenek 2003). PGD2 has been shown to activate the thromboxane prostanoid (TP) receptors found on bronchial smooth muscle thereby causing bronchoconstriction (Armour 1989; Bochenek 2003; Pettipher 2007). Administration of ifetroban in vitro has been shown to inhibit contraction of guinea pig trachea elicited by PGD2 (Ogletree 1992) and to both preempt and reverse TP receptor-induced bronchospasm in rats and guinea pigs. Direct endobronchial application of lysine-aspirin does not decrease the levels of PGD2 and PGD2 metabolites recovered from bronchoalveolar lavage (BAL) fluids from AERD patients. However, endobronchial application of lysine-aspirin does reduce the concentration of other prostaglandins (Sladek 1994; Szczeklik 1996). Thus, PGD2 production in AERD resists suppression by aspirin.

The expression of COX-2, a relatively aspirin-resistant enzyme, is expressed by a larger percentage of MCs in bronchial biopsies from patients with AERD than in those of aspirin tolerant controls (Sousa 1997). Since global expression of COX-2 in nasal polyps is reduced in AERD relative to aspirin-tolerant controls (Picado 1999), the selective upregulation of COX-2 expression by MCs likely reflects cell-specific differences in the regulation of the COX-2 isoform. Thus, the capacity for MCs to release PGD2 in AERD during aspirin challenge may be due to their preferential utilization of COX-2 for this function. The capacity of PGD2 to recruit and activate immune effector cells, induce vasodilation, and cause bronchoconstriction would fit well with a role in the pathophysiology of AERD, especially since its production resists suppression by low-dose aspirin.

Human studies demonstrate markedly impaired COX-2-dependent synthesis of PGE2 in the sinonasal tissues of patients with AERD compared with aspirin-tolerant controls (Picado 1999; Yoshimura 2008). Previous clinical studies also strongly support a critical role of platelet-adherent granulocytes as a source of cysteinyl leukotrienes (cys-LTs) in human subjects with AERD (Laidlaw 2012). To further explore the pathogenetic consequences of a deficit in COX-2-dependent PGE2 generation, sustained PGD2 generation, and the role of platelets in AERD, mice lacking microsomal PGE2 synthase (ptges−/− mice) were developed (Liu 2012; Liu 2013). PGE2 synthase is the dominant terminal enzyme responsible for conversion of COX-2-derived PGH2 to PGE2 (Murakami 2000).

To elicit the AERD phenotype in the ptges−/− mice, six doses of an extract of allergens from the house dust mite Dermatophagoides farina (Df) were administered and the animals developed marked eosinophilic bronchovascular inflammation compared with WT controls (Liu 2012). The blood and lungs of ptges−/− mice contained markedly increased numbers of platelets adhering to granulocytes, similar to the findings in humans. When challenged by inhalation of Lysine aspirin, Df-treated ptges−/− mice exhibited significant increases in airway resistance, accompanied by increases in the levels of cys-LTs, histamine, and mouse MC protease 1 in the BAL fluid. The increase in airway resistance was sensitive to interference by zileuton or montelukast (Liu 2013), consistent with the known pharmacology of AERD in humans. Exogenous antibody-mediated platelet depletion prior to the Lys-ASA challenge completely eliminated the increases in airway resistance and cys-LTs. Moreover, deletion of TP receptors from ptges−/− mice or the administration of SQ29,548, a selective antagonist of the TP receptor, completely blocked the reaction to aspirin and the rise in cys-LTs (FIG. 1). These findings imply that signaling through TP receptors is critical for platelets to mediate the transcellular synthesis of leukotriene C4 (LTC4) during challenge with aspirin. These observations support the hypothesis that TP receptor blockade will reduce the synthesis of cys-LTs in AERD and thereby provide a new treatment modality for the disease and ease the desensitization to aspirin.

SUMMARY OF THE INVENTION

It is an object of the present invention to provide new methods of treating AERD and/or asthma.

It is an object of the invention to reduce rescue medications needed as a result of an aspirin-induced reaction in a human patient suffering from AERD.

It is another object of the invention to reduce the symptoms of aspirin desensitization in AERD patients.

It accordance with the above object and others, the present invention is directed in part to providing a method of treating and/or preventing AERD or asthma in human patients by administration of a therapeutically effective amount of a thromboxane receptor antagonist. Preferably, the therapeutically effective amount of thromboxane receptor antagonist is sufficient to provide a plasma concentration of the thromboxane receptor antagonist of about 0.1 ng/ml to about 10,000 ng/ml, preferably from about 1.0 ng/ml to about 6000 ng/ml, or from about 40 ng/ml to about 3500 ng/ml, or from about 300 ng/ml to about 2500 ng/ml.

In certain embodiments, the thromoboxane receptor antagonist is a thromboxane $A_2$ receptor antagonist to a human patient(s). In preferred embodiments, the thromboxane $A_2$ antagonist is [1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid (Ifetroban), or pharmaceutically acceptable salts thereof. In certain preferred embodiments, the thromboxane $A_2$ receptor antagonist is ifetroban or a pharmaceutically acceptable salt thereof (e.g., ifetroban sodium) and the dose administered orally to human patients is from about in a daily dose from about 25 mg to about 400 mg. In such embodiments, the patient(s) will (preferably) require a reduced amount of rescue medications as compared to human patients who are not administered ifetroban. In certain preferred embodiments, the ifetroban is administered orally in an amount from about 150 mg to about 400 mg, from about 200 mg to about 300 mg, and in certain embodiments most preferably about 200 mg. In certain preferred embodiments, the ifetroban is ifetroban sodium.

The present invention is further directed in part to providing a method for treating and/or preventing AERD or asthma by administration of a therapeutically effective amount of [1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid, monosodium salt (Ifetroban Sodium) to a human patient(s). Preferably, the therapeutically effective amount provides a plasma concentration of the Ifetroban of about 0.1 ng/ml to about 10,000 ng/ml, preferably from about 1.0 ng/ml to about 6000 ng/ml, or from about 40 ng/ml to about 3500 ng/ml, or from about 300 ng/ml to about 2500 ng/ml. In certain preferred embodiments, the thromboxane $A_2$ receptor antagonist is ifetroban or a pharmaceutically acceptable salt thereof (e.g., ifetroban sodium) and the dose administered orally to human patients is from about in a daily dose from about 25 mg to about 400 mg. In such embodiments, the patient(s) will (preferably) require a reduced amount of rescue medications as compared to human patients who are not administered ifetroban. In certain preferred embodiments, the ifetroban is administered orally in an amount from about 150 mg to about 400 mg, from about 200 mg to about 300 mg, and in certain embodiments most preferably about 200 mg. In certain preferred embodiments, the ifetroban is ifetroban sodium.

In accordance with the above objects, the present invention provides for methods of preventing, reversing or treating a symptom associated with AERD or asthma including but not limited to nasal congestion (or stuffiness), eye watering, eye redness, coughing, wheezing, chest tightness; frontal headache, sensation of sinus pain, flushing, rash, hives, nausea, abdominal cramping, a general feeling of malaise, dizziness, difficulty breathing, and combinations of any of the foregoing by the administration of a therapeutically effective amount of a thromboxane receptor antagonist (preferably, a thromboxane $A_2$ receptor antagonist) to a patient in need thereof. In certain preferred embodiments, the therapeutically effective amount of a thromboxane $A_2$ receptor antagonist provides a plasma concentration of the thromboxane $A_2$ receptor antagonist of about 0.1 ng/ml to about 10,000 ng/ml, wherein the desired plasma concentration results in the patient experiencing a lessening of said symptom(s). In preferred embodiments, the thromboxane $A_2$ antagonist is [1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid (Ifetroban), or pharmaceutically acceptable salts thereof. In another preferred embodiment, the thromboxane receptor antagonist is [1S-(1α,2α,3α,4α)]-2-[[3-[4-[(Pentylamino)carbonyl]-2-oxazolyl]-7-oxabicyclo[2.2.1]hept-2-yl]methyl]-benzenepropanoic acid, monosodium salt (Ifetroban Sodium). In certain preferred embodiments, the thromboxane $A_2$ receptor antagonist is ifetroban or a pharmaceutically acceptable salt thereof (e.g., ifetroban sodium) and the dose administered orally to human patients is from about 150 mg/day to about 400 mg/day, administered in one dose or divided doses. In certain preferred embodiments, the thromboxane $A_2$ receptor antagonist is ifetroban sodium and the dose is about 200 mg/day when administered orally to a human patient(s) suffering from AERD and/or asthma.

The invention is also directed in part to a method of reducing rescue medications as a result of an aspirin-induced reaction in a human patient(s) suffering from AERD, comprising administering ifetroban or a pharmaceutically acceptable salt thereof in a daily dose from about 25 mg to about 400 mg. In such embodiments, the patient(s) will (preferably) require a reduced amount of rescue medications as compared to human patients who are not administered ifetroban. In certain preferred embodiments, the ifetroban is administered orally in an amount from about 150 mg to about 400 mg, from about 200 mg to about 300 mg, and in certain embodiments most preferably about 200 mg. In certain preferred embodiments, the ifetroban is ifetroban sodium.

The invention is also directed in part to a method of reducing the symptoms of aspirin desensitization in a human AERD patient(s), comprising rescue medications as a result of an aspirin-induced reaction in a human patient(s) suffering from AERD, comprising orally administering ifetroban or a pharmaceutically acceptable salt thereof in a daily dose from about 25 mg to about 400 mg. In such embodiments, the patient(s) will (preferably) require a reduced amount of rescue medications as compared to human patients who are not administered ifetroban. In certain preferred embodiments, the ifetroban is administered orally in an amount from about 150 mg to about 400 mg, from about 200 mg to about 300 mg, and in certain embodiments most preferably about 200 mg. In certain preferred embodiments, the ifetroban is ifetroban sodium.

In any of the above methods, the thromboxane $A_2$ receptor antagonist may be ifetroban or a pharmaceutically acceptable salt thereof (e.g., ifetroban sodium) in a daily dose of about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, and about 400 mg. The daily dose may be administered once daily, twice daily, three times daily, or four times daily.

The phrase "therapeutically effective amount" refers to that amount of a substance that produces some desired local or systemic effect at a reasonable benefit/risk ratio applicable to any treatment. The effective amount of such substance will vary depending upon the subject and disease condition being treated, the weight and age of the subject, the severity of the disease condition, the manner of administration and the like, which can readily be determined by one of ordinary skill in the art.

The term "thromboxane $A_2$ receptor antagonist" as used herein refers to a compound that inhibits the expression or activity of a thromboxane receptor by at least or at least about 30%, 35%, 40%, 45%, 50%, 55%, 60%, 65%, 70%, 75%, 80%, 85%, 90%, 95%, 96%, 97%, 98%, 99%, or 100% in a standard bioassay or in vivo or when used in a therapeutically effective dose. In certain embodiments, a thromboxane $A_2$ receptor antagonist inhibits binding of thromboxane $A_2$ to the receptor. Thromboxane $A_2$ receptor antagonists include competitive antagonists (i.e., antagonists that compete with an agonist for the receptor) and non-competitive antagonists. Thromboxane $A_2$ receptor antagonists include antibodies to the receptor. The antibodies may be monoclonal. They may be human or humanized antibodies. Thromboxane $A_2$ receptor antagonists also include thromboxane synthase inhibitors, as well as compounds that have both thromboxane $A_2$ receptor antagonist activity and thromboxane synthase inhibitor activity.

BRIEF DESCRIPTION OF THE DRAWINGS

FIG. 1 depicts the deletion or blockade of TP receptors attenuates aspirin sensitivity in PGE2-deficient mice. (A) Peak change in RL occurring in response to Lys-ASA challenge of ptges−/− or ptges/tpr−/− (DKO) mice 24 h after their final treatment with PBS or Df. (B) Peak change in RL in ptges−/− mice receiving two doses of the TP receptor selective antagonist SQ29.548 prior to challenge with Lys-ASA. (C) Levels of cys-LTs, mMCP-1, and histamine in BAL fluids from the same mice as in (B). Results are from 10 mice/group. (Adapted from Liu 2013).

DETAILED DESCRIPTION OF THE INVENTION

The discovery and development of thromboxane $A_2$ receptor antagonists has been an objective of many pharmaceutical companies for approximately 30 years (see, Dogne J-M, et al., Exp. Opin. Ther. Patents 11: 1663-1675 (2001)). Certain individual compounds identified by these companies, either with or without concomitant thromboxane $A_2$ synthase inhibitory activity, include ifetroban (BMS), ridogrel (Janssen), terbogrel (BI), UK-147535 (Pfizer), GR 32191 (Glaxo), and S-18886 (Servier). Preclinical pharmacology has established that this class of compounds has effective antithrombotic activity obtained by inhibition of the thromboxane pathway. These compounds also prevent vasoconstriction induced by thromboxane $A_2$ and other prostanoids that act on the thromboxane $A_2$ receptor within the vascular bed, and thus may be beneficial for use in preventing and/or treating hepatorenal syndrome and/or hepatic encephalopathy.

Suitable thromboxane $A_2$ receptor antagonists for use in the present invention may include, for example, but are not limited to small molecules such as ifetroban (BMS; [1S-(1α,2α,3α,4α)]-2-[[3-[4-[(pentylamino)carbony-1]-2-oxazolyl]-7-oxabicyclo[2.2.1]hept-2 yl]methyl]benzenepropanoic acid), as well as others described in U.S. Patent Application Publication No. 2009/0012115, the disclosure of which is hereby incorporated by reference in its entirety.

Additional thromboxane $A_2$ receptor antagonists suitable for use herein are also described in U.S. Pat. No. 4,839,384 (Ogletree); U.S. Pat. No. 5,066,480 (Ogletree, et al.); U.S. Pat. No. 5,100,889 (Misra, et al.); U.S. Pat. No. 5,312,818 (Rubin, et al.); U.S. Pat. No. 5,399,725 (Poss, et al.); and U.S. Pat. No. 6,509,348 (Ogletree), the disclosures of which are hereby incorporated by reference in their entireties. These may include, but are not limited to, interphenylene 7-oxabicyclo-heptyl substituted heterocyclic amide prostaglandin analogs as disclosed in U.S. Pat. No. 5,100,889, including:

[1S-(1α, 2α, 3α, 4α)]-2-[[3-[4-[[(4-cyclo-hexylbutyl)amino]carbonyl]-2-oxazolyl]-7-oxabicyclo[2.2.1]-hept-2-yl]methyl]benzenepropanoic acid (SQ 33,961), or esters or salts thereof;

[1S-(1α, 2α, 3α, 4α)]-2- [[3-[4-[[[(4-chloro- phenyl)-butyl]amino]carbonyl]-2-oxazolyl]-7-oxabicyclo[2.2.1] hept-2-yl]methyl]benzenepropanoic acid or esters, or salts thereof;

[1S-(1α, 2α, 3α, 4α)]-3-[[3-[4-[[(4-cycloh-exylbutyl)-amino]carbonyl]-2-oxazolyl]-7-oxabicyclo]2.2.1]hept-2-yl] benzene acetic acid, or esters or salts thereof;

[1S-(1α, 2α, 3α, 4α)]-2-[[3-[4-[[(4-cyclohexyl-butyl) amino]carbonyl]-2-oxazolyl]-7-oxabicyclo[2.2.1]hept-2-yl] methyl]phenoxy]acetic acid, or esters or salts thereof;

[1S-(1α, 2α, 3α, 4α]-2-[[3-[4-[[(7,7-dime-thyloctyl)-amino]carbonyl]-2-oxazolyl]-7-oxabicyclo[2.2.1]hept-2-yl]-methyl]benzenepropanoic acid, or esters or salts thereof.

7-oxabicycloheptyl substituted heterocyclic amide prostaglandin analogs as disclosed in U.S. Pat. No. 5,100,889, issued Mar. 31, 1992, including [1S-[1α, 2α (Z), 3α, 4α)]-6-[3-[4-[[(4-cyclohexylbutyl)amino]-carbonyl]-2-oxazolyl]-7-oxabicyclo[2.2.1]hept-2-yl]-4-hexenoic acid, or esters or salts thereof;

[1S-[1α, 2α (Z), 3α, 4α)]]-6-[3-[4-[[(4-cyclohexyl-butyl) amino]carbonyl]-2-thiazolyl]-7-oxabicyclo[2.2.1]hept-2-yl]-4-hexenoic acid, or esters or salts thereof;

[1S-[1α, 2α (Z), 3α, 4α)]]-6-[3-[4-[[(4-cyclohexyl-butyl) methylamino]carbonyl]-2-oxazolyl]-7-oxabicyclo-[2.2.1] hept-2-yl]-4-hexenoic acid, or esters or salts thereof;

[1S-[1α, 2α (Z), 3α, 4α)]]-6-[3-[4-[(1-pyrrolidinyl)-carbonyl]-2-oxazolyl]-7-oxabicyclo[2.2.1]hept-2-yl]-4-hexenoic acid, or esters or salts thereof;

[1S-[1α, 2α (Z), 3α, 4α)]]-6-[3-[4-[(cyclohexylamino)-carbonyl]-2-oxazolyl]-7-oxabicyclo[2.2.1]hept-2-yl-4-hexenoic acid or esters or salts thereof;

[1S-[1α, 2α (Z), 3α, 4α)]]-6-[3-[4-[[(2-cyclohexyl-ethyl) amino]carbonyl]-2-oxazolyl]-7-oxabicyclo[2.2.1]hept-2-yl]-4-hexenoic acid, or esters or salts thereof;

[1S-[1α, 2α (Z), 3α, 4α)]]-6-[3-[4-[[[2-(4-chloro-phenyl) ethyl]amino]carbonyl]-2-oxazolyl]-7-oxabicyclo-[2.2.1] hept-2-yl]-4-hexenoic acid, or esters or salts thereof;

[1S-[1α, 2α (Z), 3α, 4α)]-6-[3-[4-[[(4-chlorophenyl)-amino]carbonyl]-2-oxazolyl]-7-oxabicyclo[2.2.1]hept-2-yl]-4-hexenoic acid, or esters or salts thereof;

[1S-[1α, 2α (Z), 3α, 4α)]]-6-[3-[4-[[[4-(4-chloro-phenyl) butyl]amino]carbonyl]-2-oxazolyl]-7-oxabicyclo-[2.2.1] hept-2-yl]-4-hexenoic acid, or esters or salts thereof;

[1S-[11α, 2α (Z), 3α, 4α)]]-6-[3-[4.alpha.-[[-(6-cyclo-hexyl-hexyl)amino]carbonyl]-2-oxazolyl]-7-oxabicyclo [2.2.1]hept-2-yl]-4-hexenoic acid, or esters, or salts thereof;

[1S-[1α, 2α (Z), 3α, 4α)]]-6-[3-[4-[[(6-cyclohexyl-hexyl)amino]carbonyl]-2-oxazolyl]-7-oxabicyclo[2.2.1]hept-2-yl]-4-hexenoic acid, or esters or salts thereof;

[1S-[1α, 2α (Z), 3α, 4α]]-6-[3-[4-[(propylamino)-carbonyl]-2-oxazolyl]-7-oxabicyclo[2.2.1]hept-2-yl]-4-hexenoic acid, or esters or salts thereof

[1S-[1α, 2α (Z), 3α, 4α)]]-6-[3-[4-[[(4-butylphenyl)-amino]carbonyl]-2-oxazolyl]-7-oxabicyclo[2.2.1]hept-2-yl]-4-hexenoic acid, or esters or salts thereof;

[1S-[1α, 2α (Z), 3α, 4α)]]-6-[3-[4-[(2,3-dihydro-1H-indo1-1-yl)carbonyl]-2-oxazolyl]-7-oxabicyclo(2.2.1]hept-2-yl]-4-hexenoic acid, or esters or salts thereof;

[1S-[1α, 2α (Z), 3α, 4α)]]-6-[3-[4-[[(4-cyclohexyl-butyl)amino]carbonyl]-2-oxazolyl]-7-oxabicyclo[2.2.1]hept-2-yl]-N-(phenylsulfonyl)-4-hexenamide;

[1S-[11α, 2α (Z), 3α, 4α)]]-6-[3-[4-[[(4-cyclohexyl-butyl)amino]carbonyl]-2-oxazolyl]-N-(methylsulfonyl)-7-oxabicyclo[2-.2.1]hept-2-yl1-4-hexenamide;

[1S-[1α, 2α (Z), 3α, 4α)]]-7-[3-[4-[[(4-cyclohexyl-butyl)amino]carbonyl]-2-oxazolyl]-7-oxabicyclo (2.2.1]hept-2-yl]-5-heptenoic acid, or esters or salts thereof;

[1S-[1α, 2α (Z), 3α, 4α)]]-6-[3-[4-[[(4-cyclohexyl-butyl)amino]carbonyl]-1H-imidazol-2-yl]-7-oxabicyclo-[2.2.1]hept-2-yl]-4-hexenoic acid or esters or salts thereof;

[1S-[1a, 2a, 3α, 4α)]-6-[3-[4-[[(7,7-dimethyloctyl)-amino]carbonyl]-2-oxazolyl]-7-oxabicyclo[2.2.1]hept-2-yl]-4-hexenoic acid, or esters or salts thereof;

[1S-[1α, 2α(E), 3α, 4α)]]-6-[3-[4-[[(4-cyclohexyl-butyl)amino]carbonyl]-2-oxazolyl]-7-oxabicyclo[2.2.1]hept-2-yl]-4-hexenoic acid;

[1S-[1α, 2α, 3α, 4α)]-3-[4-[[(4-(cyclohexylbutyl)-amino]carbonyl]-2-oxazolyl]-7-oxabicyclo[2.2.1]heptane-2-hexanoic acid or esters or salts thereof,

[1S-[1α, 2α(Z), 3α, 4α)]]-6-[3-[4-[[(4-cyclohexyl-butyl)amino]carbonyl]-2-oxazolyl]-7-oxabicyclo-[2.2.1]hept-2-yl]-4-hexenoic acid, or esters or salts thereof;

7-oxabicycloheptane and 7-oxabicycloheptene compounds disclosed in U.S. Pat. No. 4,537,981 to Snitman et al, the disclosure of which is hereby incorporated by reference in its entirety, such as [1S-(1α, 2α(Z), 3α(1E, 3S*, 4R*), 4α)]]-7-[3-(3-hydroxy-4-phenyl-1-pentenyl)-7-oxabicyclo [2.2.1]hept-2-yl]-5-heptenoic acid (SQ 29,548); the 7-oxabicycloheptane substituted aminoprostaglandin analogs disclosed in U.S. Pat. No. 4,416,896 to Nakane et al, the disclosure of which is hereby incorporated by reference in its entirety, such as [1S-[1α, 2α(Z), 3α, 4α)]]-7-[3-[[2-(phenylamino)carbonyl]-hydrazino]methyl]-7-oxabicyclo [2.2.1]hept-2-yl]-5-heptenoic acid; the 7-oxabicycloheptane substituted diamide prostaglandin analogs disclosed in U.S. Pat. No. 4,663,336 to Nakane et al, the disclosure of which is hereby incorporated by reference in its entirety, such as, [1S-[1α, 2α(Z), 3α, 4α)]]-7-[3-[[[[(1-oxoheptyl)amino]-acetyl]amino]methyl]-7-oxabicyclo[2.2.1]hept-2-yl]-5-heptenoic acid and the corresponding tetrazole, and [1S-[1α, 2α(Z), 3α,4α)]]-7- [3-[[[[(4-cyclohexyl-1-oxobutyl)-amino]acetyl]amino]methyl]-7-oxabicyclo]2.2.1]hept-2-yl]-5-heptenoic acid;

7-oxabicycloheptane imidazole prostaglandin analogs as disclosed in U.S. Pat. No. 4,977,174, the disclosure of which is hereby incorporated by reference in its entirety, such as [1S-[1α, 2α(Z), 3α, 4α)]]-6-[3- [[4-(4-cyclohexyl-1-hydroxybutyl)-1H-imidazole-1-yl]methyl]-7-oxabicyclo [2.2.1]hept-2-yl]-4-hexenoic acid or its methyl ester;

[1S-[1α, 2α(Z), 3α, 4α)]]-6-[3-[[4-(3-cyclohexyl-propyl)-1H-imidazol-1-yl]methyl]-7-oxabicyclo[2.2.1]hept-2-yl]-4-hexenoic acid or its methyl ester;

[1S-[1α, 2α(X(Z), 3α, 4α)]]-6-[3-[[4-(4-cyclohexyl-1-oxobutyl)-1H-imidazol-1-yl]methyl]-7-oxabicyclo[2.2.1]hept-2-yl]-4-hexenoic acid or its methyl ester;

[1S-[1α, 2α(Z), 3α, 4α]]-6-[3-(1H-imidazol-1-ylmethyl)-7-oxabicyclo[2.2.1]hept-2-yl]-4-hexenoic acid or its methyl ester; or

[1S-[1α, 2α(Z), 3α, 4α)]]-6-[3-[[4-[[(4-cyclohexyl-butyl)amino]carbonyl]-1H-imidazol-1-yl]methyl]-7-oxabicyclo-[2.2.1]- hept-2-yl]-4-hexenoic acid, or its methyl ester;

The phenoxyalkyl carboxylic acids disclosed in U.S. Pat. No. 4,258,058 to Witte et al, the disclosure of which is hereby incorporated by reference in its entirety, including 4-[2-(benzenesulfamido)ethyl]phenoxy-acetic acid (BM 13,177-Boehringer Mannheim), the sulphonamidophenyl carboxylic acids disclosed in U.S. Pat. No. 4,443,477 to Witte et al, the disclosure of which is hereby incorporated by reference in its entirety, including 4-[2-(4-chlorobenzene-sulfonamido)ethyl]-phenylacetic acid (BM 13,505, Boehringer Mannheim), the arylthioalkylphenyl carboxylic acids disclosed in U.S. Pat. No. 4,752,616, the disclosure of which is hereby incorporated by reference in its entirety, including 4-(3-((4-chlorophenyl)sulfonyl)propyl)benzene acetic acid.

Other examples of thromboxane $A_2$ receptor antagonists suitable for use herein include, but are not limited to vapiprost (which is a preferred example), (E)-5-[[[(pyridinyl)]3-(trifluoromethyl)phenyl]methylene]amino]-oxy]pentanoic acid also referred to as R68,070-Janssen Research Laboratories, 3-[1-(4-chlorophenylmethyl)-5-fluoro-3-methylindol-2-yl]-2,-2-dimethylpropanoic acid [(L-655240 Merck-Frosst) Eur. J. Pharmacol. 135(2):193, Mar. 17, 87], 5(Z)-7-([2,4,5-cis]-4-(2-hydroxyphenyl)-2-trifluoromethyl-1,3-dioxan-5-yl)heptenoic acid (ICI 185282, Brit. J. Pharmacol. 90 (Proc. Suppl):228 P-Abs, March 87), 5(Z)-7-[2, 2-dimethyl-4-phenyl-1,3-dioxan-cis-5-yl]heptenoic acid (ICI 159995, Brit. J. Pharmacol. 86 (Proc. Suppl):808 P-Abs., December 85), N,N'-bis[7-(3-chlorobenzeneamino-sulfony-1)-1,2,3,4-tetrahydro-isoquinolyl]disulfonylimide (SKF 88046, Pharmacologist 25(3):116 Abs., 117 Abs, August 83), (1.alpha.(Z)-2.beta., 5.alpha.]-(+)-7-[5-[[(1,1'-biphenyl)-4-yl]-methoxy]-2-(4-morpholinyl)-3- oxocyclopentyl]-4-heptenoic acid (AH 23848 -Glaxo, Circulation 72(6):1208, December 85, levallorphan allyl bromide (CM 32,191 Sanofi, Life Sci. 31 (20-21):2261, Nov. 15, 82), (Z,2-endo-3-oxo)-7-(3-acetyl-2-bicyclo [2.2.1]heptyl5-hepta-3Z-enoic acid, 4-phenyl-thiosemicarbazone (EP092- Univ. Edinburgh, Brit. J. Pharmacol. 84(3):595, March 85); GR 32,191 (Vapiprost)-[1R-[1.alpha.(Z), 2.beta., 3.beta., 5.alpha.]]-(+)-7-[5-([1,1'-biphenyl]-4-ylmethoxy)-3-hydroxy-2-(1-piperidinyl)cyclopentyl]-4-heptenoic acid; ICI 192,605-4(Z)-6-[(2,4,5-cis)2-(2-chlorophenyl)-4-(2-hydroxyphenyl)-1,3-dioxan-5-yl]hexenoic acid; BAY u 3405 (ramatroban)-3-[[(4-fluorophenyl)-sulfonyl]amino]-1,2,3,4-tetrahydro-9H-c-arbazole-9-propanoic acid; or ONO 3708-7-[2.alpha., 4.alpha.-(dimethylmethano)-6.beta.-(2-cyclopentyl-2.beta.-hydroxyacetami-do)-1.alpha.-cyclohexyl]-5 (Z)-heptenoic acid; (.+−.)(5Z)-7-[3-endo-((phenylsulfonyl) amino]-bicyclo[2.2.1]hept-2-exo-yl]-heptenoic acid (S-1452, Shionogi domitroban.); (−)6,8-difluoro-9-p-methylsulfonylben-zyl-1,2,3,4-tetrahydrocarbazol-1-yl-acetic acid (L670596, Merck) and (3-[1-(4-chlorobenzyl)-5-fluoro-3-methyl-indol-2-yl]-2,2-dimethylpropanoic acid (L655240, Merck).

The preferred thromboxane $A_2$ receptor antagonist of the present invention is ifetroban or any pharmaceutically acceptable salts thereof.

In certain preferred embodiments the preferred thromboxane $A_2$ receptor antagonist is ifetroban sodium (known chemically as [1S-(1α,2α,3α,4α)]-2-[[3-[4-[(Pentylamino) carbonyl]-2-oxazolyl]-7-oxabicyclo[2.2.1]hept-2-yl] methyl]-benzenepropanoic acid, monosodium salt.

In certain embodiments, the AERD and/or asthma is treated via the administration of a thromboxane receptor antagonist (e.g., a thromboxane $A_2$ receptor antagonist) ranging from about 0.1 ng/ml to about 10,000 ng/ml. Preferably, the plasma concentration of thromboxane receptor antagonist ranges from about 1 ng/ml to about 1,000 ng/ml, preferably from about 1.0 ng/ml to about 6000 ng/ml, or from about 40 ng/ml to about 3500 ng/ml, or from about 300 ng/ml to about 2500 ng/ml.

In certain preferred embodiments, the thromboxane $A_2$ receptor antagonist is ifetroban or a pharmaceutically acceptable salt thereof (e.g., ifetroban sodium) and the dose administered orally to human patients is from about 150 mg/day to about 400 mg/day, administered in one dose or divided doses. In certain preferred embodiments, the thromboxane $A_2$ receptor antagonist is ifetroban sodium and the dose is about 200 mg/day when administered orally to a human patient(s) suffering from AERD and/or asthma.

When the thromboxane $A_2$ receptor antagonist is ifetroban, the desired plasma concentration for providing a therapeutic effect for the treatment of AERD and/or asthma should be greater than about 10 ng/mL (ifetroban free acid). Some therapeutic effect of thromboxane $A_2$ receptor antagonist, e.g., ifetroban, may be seen at concentrations of greater than about 1 ng/mL.

The dose administered must be carefully adjusted according to age, weight and condition of the patient, as well as the route of administration, dosage form and regimen and the desired result.

However, in order to obtain the desired plasma concentration of thromboxane $A_2$ receptor antagonists, daily doses of the thromboxane $A_2$ receptor antagonists ranging from about 0.1 mg to about 5000 mg should be administered. Preferably, the daily dose of thromboxane $A_2$ receptor antagonists ranges from about 1 mg to about 1000 mg; about 10 mg to about 1000 mg; about 50 mg to about 500 mg; about 100 mg to about 500 mg; about 200 mg to about 500 mg; about 300 mg to about 500 mg; and about 400 mg to about 500 mg per day.

In certain preferred embodiments, a daily dose of ifetroban sodium from about 10 mg to about 250 mg (ifetroban free acid amounts) will produce effective plasma levels of ifetroban free acid.

The thromboxane $A_2$ receptor antagonists of the present invention may be administered by any pharmaceutically effective route. For example, the thromboxane $A_2$ receptor antagonists may be formulated in a manner such that they can be administered orally, intranasally, rectally, vaginally, sublingually, buccally, parenterally, or transdermally, and, thus, be formulated accordingly.

In certain embodiments, the thromboxane $A_2$ receptor antagonists may be formulated in a pharmaceutically acceptable oral dosage form. Oral dosage forms may include, but are not limited to, oral solid dosage forms and oral liquid dosage forms.

Oral solid dosage forms may include, but are not limited to, tablets, capsules, caplets, powders, pellets, multiparticulates, beads, spheres and any combinations thereof. These oral solid dosage forms may be formulated as immediate release, controlled release, sustained (extended) release or modified release formulations.

The oral solid dosage forms of the present invention may also contain pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof.

Depending on the desired release profile, the oral solid dosage forms of the present invention may contain a suitable amount of controlled-release agents, extended-release agents, modified-release agents.

Oral liquid dosage forms include, but are not limited to, solutions, emulsions, suspensions, and syrups. These oral liquid dosage forms may be formulated with any pharmaceutically acceptable excipient known to those of skill in the art for the preparation of liquid dosage forms. For example, water, glycerin, simple syrup, alcohol and combinations thereof.

In certain embodiments of the present invention, the thromboxane $A_2$ receptor antagonists may be formulated into a dosage form suitable for parenteral use. For example, the dosage form may be a lyophilized powder, a solution, suspension (e.g., depot suspension).

In other embodiments, the thromboxane receptor antagonists may be formulated into a topical dosage form such as, but not limited to, a patch, a gel, a paste, a cream, an emulsion, liniment, balm, lotion, and ointment.

A significant proportion of patients that suffer from asthma take one or more medications on a daily (chronic) basis in order to prevent or attenuate symptoms of asthma. Such drugs include corticosteroids (including but not limited to inhaled corticosteroids), Cromolyn, Omalizumab, short or long-acting beta-2 agonists (typically inhaled), leukotriene modifiers (e.g., zafirlukast (sold under the trademark Accolate®), montelukast (sold under the trademark Singulair®), and zileuton (sold under the trademark Zyflo®)), and theophylline, and a combination drug that includes a steroid and a long-acting bronchodilator drug, fluticasone propionate and salmeterol, sold under the trademark Advair®. Inhaled steroid medications include but are not limited to the following: flunisolide, sold under the trademark Aerobid®, mometasone furoate, sold under the trademark Asmanex®, triamcinolone acetonide, sold under the trademark Azmacort®, mometasone furoate and formoterol fumarate dihydrate, sold under the trademark Dulera® (a combination drug that also includes a long-acting bronchodilator drug), fluticasone propionate, sold under the trademark Flovent®, budesonide, sold under the trademark Pulmicort®, formoterol fumarate dihydrate and budesonide, sold under the trademark Symbicort® (a combination drug that includes a steroid and a long-acting bronchodilator drug), beclomethasone dipropionate, sold under the trademark Qvar®, and the like. Inhaled steroids come in three forms: the metered dose inhaler (MDI), dry powder inhaler (DPI), and nebulizer solutions. Omalizumab (sold under the trademark Xolair®, Roche/Genentech and Novartis) is a humanized antibody originally designed to reduce sensitivity to inhaled or ingested allergens, especially in the control of moderate to severe allergic asthma, which does not respond to high doses of corticosteroids. In certain embodiments, the present method of treatment further contemplates combination therapy comprising administering a thromboxane receptor antagonist and one or more of the above drugs to a human patient suffering from AERD and/or asthma.

DETAILED DESCRIPTION OF THE PREFERRED EMBODIMENTS

The following examples are not meant to be limiting and represent certain embodiments of the present invention.

EXAMPLE 1

In this example, ifetroban sodium tablets are prepared with the following ingredients listed in Table 1:

TABLE 1

| Ingredients | Percent by weight |
| --- | --- |
| Na salt of Ifetroban | 35 |
| Mannitol | 50 |
| Microcrystalline Cellulose | 8 |
| Crospovidone | 3.0 |
| Magnesium Oxide | 2.0 |
| Magnesium Stearate | 1.5 |
| Colloidal Silica | 0.3 |

The sodium salt of ifetroban, magnesium oxide, mannitol, microcrystalline cellulose, and crospovidone is mixed together for about 2 to about 10 minutes employing a suitable mixer. The resulting mixture is passed through a #12 to #40 mesh size screen. Thereafter, magnesium stearate and colloidal silica are added and mixing is continued for about 1 to about 3 minutes.

The resulting homogeneous mixture is then compressed into tablets each containing 35 mg, ifetroban sodium salt.

EXAMPLE II

In this example, 1000 tablets each containing 400 mg of Ifetroban sodium are produced from the following ingredients listed in Table 2:

TABLE 2

| Ingredients | Amount |
| --- | --- |
| Na salt of Ifetroban | 400 gm |
| Corn Starch | 50 g |
| Gelatin | 7.5 g |
| Microcrystalline Cellulose (Avicel) | 25 g |
| Magnesium Stearate | 2.5 g |

EXAMPLE III

In this example. An injectable solution of ifetroban sodium is prepared for intravenous use with the following ingredients listed in Table 3:

TABLE 3

| Ingredients | Amount |
| --- | --- |
| Ifetroban Sodium | 2500 mg |
| Methyl Paraben | 5 mg |
| Propyl Paraben | 1 mg |
| Sodium Chloride | 25,000 mg |
| Water for injection q.s. | 5 liter |

The sodium salt of ifetroban, preservatives and sodium chloride are dissolved in 3 liters of water for injection and then the volume is brought up to 5 liters. The solution is filtered through a sterile filter and aseptically filled into pre-sterilized vials which are then closed with pre-sterilized rubber closures. Each vial contains a concentration of 75 mg of active ingredient per 150 ml of solution.

EXAMPLE IV

Example IV is a multicenter, double-blind, randomized, placebo-controlled trial to determine the safety of oral ifetroban in patients with a history of aspirin exacerbated respiratory disease (AERD).

The eligible subjects were randomized (3:1 active to placebo) in this 7-day study which consisted of a screening, treatment and follow-up period. Any subject receiving at least a partial dose of IMP were not replaced and included in the study analysis. Of 19 subjects enrolled and randomized to study treatment, 14 (74%) were randomized to the ifetroban group and 5 (26%) to the placebo group. Of those 14 randomized to ifetroban, 12 (86%) subjects were treated and 100% of those treated completed treatment. Of 5 subjects randomized to placebo, 4 (80%) started treatment and 100% completed treatment. All treated subjects were analyzed for safety and efficacy variables.

A placebo treatment arm was included in this study to provide data on the spontaneous response rate of AERD subjects, as well as to help identify any safety or efficacy signals in the subjects receiving ifetroban. In numerous trials, subjects with asthma assigned to placebo have demonstrated improvement in symptoms, quality of life, and even in lung function, such as FEV1. In general, the placebo effect in asthma can be as great as 30 to 50% depending on which endpoint is chosen (Castro, 2007; *Placebo versus Best-Available-Therapy Control Group in Clinical Trials for Pharmacologic Therapies. Proceedings of the American Thoracic Society*, 570-573).

All individuals with AERD will experience a clinical reaction to aspirin, most often at a dose of 81 mg or below. By utilizing a modified Scripps Institute protocol (Hope, Woessner, Simon, & Stevenson, 2009), limiting the study to individuals with stable asthma and no history of life-threatening reaction to COX inhibitors and administering the cysteinyl leukotriene receptor 1 (Cys-LT1) antagonist montelukast to all individuals undergoing the challenge/desensitization, the procedure could safely be done in an ambulatory/outpatient clinic setting. The results of a study published in 2006 (White, Ludington, Mehra, Stevenson, & Simon, 2006), demonstrated that leukotriene modifier drugs, like montelukast, had a significant effect in protecting the lower airways from severe reactions (P=0.004) in subjects undergoing aspirin challenge/desensitization. Thus, montelukast substantially increases the safety of aspirin challenge/desensitization and it is the standard of care to use montelukast as a pre-treatment for subjects with AERD undergoing a planned aspirin challenge/desensitization. Because montelukast does not inhibit CYP2C9 or CYP3A4, montelukast was not expected to affect the elimination of ifetroban.

The primary objective of this study was to determine the safety of oral ifetroban compared to placebo as measured by a ≥20% decrease in Forced Expiratory Volume in 1 second (FEV1) compared to baseline following a dose of Investigational Medicinal Product (IMP) (Study Day 1) or following a dose of IMP but prior to initiation of the aspirin challenge. Secondary objectives were: (i) to determine the safety of oral ifetroban compared to placebo as measured by peak Nasal Inspiratory Flow Rate (NIFR) compared to baseline following a dose of IMP (Study Day 1) or following a dose of IMP but prior to initiation of the aspirin challenge; (ii) to determine the safety of oral ifetroban compared to placebo as measured by the change in Total Nasal Symptom Score (TNSS) compared to baseline following a dose of IMP (Study Day 1) or following a dose of IMP but prior to initiation of the aspirin challenge; (iii) to determine the safety and tolerability of oral ifetroban compared to placebo as measured by treatment-emergent adverse events; (iv) to determine the efficacy of oral ifetroban compared to placebo in decreasing the respiratory reaction to oral aspirin as measured by the change in FEV1 compared to baseline during the aspirin challenge; (v) to determine the efficacy of oral ifetroban compared to placebo in decreasing the respiratory reaction to oral aspirin as measured by the change in NIFR compared to baseline during the aspirin challenge; (vi) to determine the efficacy of oral ifetroban compared to placebo in decreasing the respiratory reaction to oral aspirin as measured by the change in TNSS compared to baseline during the aspirin challenge; (vii) to determine the efficacy of oral ifetroban compared to placebo in decreasing the respiratory reaction to oral aspirin as measured by the amount of rescue medication during the aspirin challenge; (viii) to determine the efficacy of oral ifetroban compared to placebo in decreasing respiratory sensitivity to COX-1 inhibition as measured by the aspirin desensitization dose level; and (ix) to determine the efficacy of oral ifetroban compared to placebo as measured by the number of asthmatic reactions during the Treatment Period.

The main criteria for inclusion in the study were adults with a history of physician-diagnosed stable asthma (FEV1 of at least 1.25 Liters (L) and 60% or better than predicted (calculated by spirometer based on gender, age, etc.) on two previous visits with no more than a 10% variation in those values, no increase in baseline dose of oral glucocorticoids for asthma for at least three months, and no history of hospitalization or emergency room visits for asthma for at least the prior six months), who have a history of nasal polyposis and have a history of at least one clinical reaction to oral aspirin or other nonselective cyclooxygenase (COX) inhibitor with features of lower (cough, chest tightness, wheezing, dyspnea) and/or upper (rhinorrhea, sneezing, nasal obstruction, conjunctival itching and discharge) airway involvement, and who are currently receiving montelukast (at least 10 mg per day, oral) or zafirlukast (at least 20 mg, twice per day, oral), with at least 1 week of therapy prior to receiving the first dose of the investigational medicinal product (IMP).

Subjects were allowed to enter the trial on the following medications: oral corticosteroids at a dose of ≤10 mg/day prednisone or prednisone equivalent, inhaled/nasal corticosteroids, inhaled long-acting β-adrenergic agonists and inhaled ipratropium; however, no modifications were allowed during the study except for a temporary increase in the dose of oral corticosteroids if asthma worsened requiring such intervention. Subjects were required to stop using short-acting β-adrenergic agonists 24 hours prior, nasal decongestants and antihistamines 48 hours prior to first dose of IMP and throughout the study unless asthma worsened requiring such intervention.

Oral, nasal, inhaled corticosteroids and inhaled long acting beta-adrenergic agonists and inhaled ipratropium were allowed to be used during the study without modification to the subject's dosing regimen if the subject entered the trial on such medications. It is believed that these medications would not mask a potential response to the aspirin challenge. Inhaled short acting beta-adrenergic agonists, nasal decongestants, and antihistamines were not allowed for specified periods prior to the study and through the initiation of the aspirin challenge as these medications may mask a potential response and thus affect the study efficacy endpoints. Warfarin, antiplatelet, or anticoagulant medications were prohibited 2 weeks prior to enrollment and during the course of the study.

The primary efficacy variable assessed was FEV1 measured by spirometry. Secondary efficacy variables included the NIFR using a Youlten meter (or similar), and the subject-completed questionnaire, Total Nasal Symptom Score (TNSS). Additional efficacy variables were the incidence of asthmatic reactions, the incidence of respiratory reactions to oral aspirin, the amount of medications used to manage an aspirin-induced reaction and the aspirin dose at which a reaction was provoked during the desensitization process.

The treatment period consisted of a phase A assessing safety and efficacy of IMP administered Day 1 and Day 2 followed by a phase B assessing safety and efficacy of IMP during the aspirin challenge on Day 2 and Day 3. Subjects experiencing a decrease in FEV1 of ≥20% during phase A would not continue to phase B of the study. The follow-up period started upon completion of the aspirin challenge and ended on Day 7 with a phone call to assess for safety. All subjects were required to be taking either oral montelukast or zafirlukast (at least 10 mg/day or 20 mg twice per day, respectively) one week prior to the study and for the duration of the study. Ifetroban was supplied as 50-mg ifetroban sodium capsules and orally administered at a dose of 200 mg every 24 hours for three consecutive days. Identically appearing placebo capsules were provided for blinding purposes and 4 capsules administered orally every 24 hours for 3 consecutive days. The duration of IMP treatment was 3 days. The study duration was 7 days.

No subject met this primary endpoint therefore all subjects continued to phase B of the study. No subject experienced a ≥20% decrease in FEV1 during the aspirin challenge (phase B). At baseline, FEV1 was comparable between treatment groups (Table 8 and Table 10). Mean changes from baseline FEV1 remained well below 20% throughout the treatment period in both treatment groups. No clear trends were observed between treatment groups. At baseline, FEV1 was comparable between treatment groups. Mean changes from baseline FEV1 remained well below 20% throughout the treatment period in both treatment groups. No clear trends were observed between treatment groups.

Safety evaluations included spirometry, NIFR, TNSS, adverse events, & vital signs. No serious adverse events (SAE) or treatment-emergent SAEs were reported.

Additional secondary objectives included evaluating the treatment groups for the proportion of subjects with a ≥25% decrease in peak NIFR (nasal inspiratory flow rate) and the proportion of subjects with a ≥25%, 50% and 75% increase in TNSS (total nasal symptom score) during phase A and phase B. The results are further described in Table 4 below:

TABLE 4

Changes from Baseline in NIFR and TNSS during Phase A and Phase B

| No. of Subjects (%) | Phase A | | Phase B | | Phase C | |
| --- | --- | --- | --- | --- | --- | --- |
| | Ifetroban n = 12 | Placebo n = 4 | Ifetroban n = 12 | Placebo n = 4 | Ifetroban n = 12 | Placebo n = 4 |
| NIFR | | | | | | |
| ≥25% decrease | 2(17) | 1(25) | 4(33) | 1(25) | 5(42) | 1(25) |
| ≥25% increase | 3(25) | 0 | 7(58) | 2(50) | 9(75) | 2(50) |
| TNSS | | | | | | |
| ≥25% increase | 0 | 0 | 3(25) | 1(25) | 3(25) | 1(25) |
| ≥25% decrease | 1(8) | 0 | 2(17) | 0 | 2(17) | 0 |

NIFR = nasal inspiratory flow rate,
TNSS = total nasal symptom score;
*Overall number of subjects may be less than the sum of subjects in phase A and phase B columns since a subject that experienced an event during phase A and phase B is counted twice.
* Overall number of subjects may be less than the sum of subjects in phase A and phase B columns since a subject that experienced an event during phase A and phase B is counted twice Overall there were 6 (38%) subjects that experienced a ≥25% decrease in peak NIFR, and 4 (25%) subjects that experienced a ≥25% increase in TNSS during the study. As expected, these events occurred mainly in phase B during the aspirin desensitization process. Five (42%) subjects receiving ifetroban and 1 (25%) subject receiving placebo experienced a ≥25% decrease in peak NIFR during the study. One subject in each treatment arm experienced a ≥25% decrease in peak NIFR during both phase A and phase B. No one experienced a ≥50% or 75% increase or decrease in TNSS during the study. No subject experienced a ≥25% increase in TNSS during phase A.

Conversely, 1 (8%) subject during phase A and 2 (17%) subjects during phase B experienced a ≥25% decrease in TNSS but only in the ifetroban arm. No subject on placebo experienced a ≥25% decrease in TNSS during the study. There were 9 (75%) subjects receiving ifetroban and 2 (50%) subjects receiving placebo that experienced a ≥25% increase in peak NIFR during the study. These increases in peak NIFR occurred mainly in phase B during the aspirin desensitization process. While no clear trends were observed in the proportion of subjects with worsening NIFR or TNSS between treatment groups, there is an observed trend in favor of the ifetroban group toward greater improvements to NIFR and TNSS during phase A and phase B.

No asthmatic reactions were reported or rescue medications used during phase A prior to aspirin initiation. For this reason, all 16 subjects treated with IMP continued to phase B. Rescue medication was only administered as a result of an aspirin-induced reaction (AIR) during the aspirin desensitization process and no subject required rescue medication outside the clinic for an asthmatic reaction throughout the 7-day study period. Two (17%) subjects on ifetroban and 1 (25%) subject on placebo did not experience an AIR during the aspirin desensitization process hence no rescue medication was administered to these 3 (19%) subjects. 1 (10%) subject on the ifetroban arm experienced an AIR yet required no rescue medication to resolve symptoms. All 3 (100) subjects on the placebo arm that experienced an AIR required rescue medications and a greater number of medications on average were needed to resolve their symptoms compared to subjects on ifetroban that experienced an AIR. The amount of rescue medication required during the aspirin challenge (phase B) was evaluated as a secondary efficacy endpoint. Subjects on the placebo arm required, on average, 7.33 rescue medications to resolve an aspirin-induced reaction (AIR), while subjects on ifetroban required a mean of 2.90 rescue medications, a 2.5 fold difference. There is a trend toward fewer rescue medications in favor of the ifetroban group. A summary of AIRs and Rescue medication use is provided in Table 5 below:

TABLE 5

Summary of AERD Phase 2a Data: AIRs and Rescue Medication Use

| No. of Subjects (%) | Ifetroban n = 12 | Placebo n = 4 | All Subjects n = 16 |
|---|---|---|---|
| Aspirin-induced Reaction (AIR) | | | |
| Yes | 10 (83) | 3 (75) | 13 (81) |
| No | 2 (17) | 1 (25) | 3 (19) |
| Required Rescue Medication* | | | |
| Yes | 9 (90) | 3 (100) | 12 (92) |
| No | 1 (10) | 0 | 1 (8) |
| Total Number of Rescue Medications | 29 | 22 | 51 |
| Mean (SD) | 2.90 (2.02) | 7.33 (3.79) | 3.92 (3.04) |
| Median* | 3 | 9 | 3 |
| Min, Max* | 0, 7 | 3, 10 | 0, 10 |

There is a trend toward fewer rescue medications in favor of the ifetroban group.

The incidence of the AIR provoked at each aspirin dose was evaluated between treatment groups and summarized in this table. All subjects who experienced an AIR reacted to a provoking dose of 60 and/or 100 mg. No reaction occurred after the 100-mg provoking dose. All initial reactions in the placebo arm occurred at the 60-mg dose while in the ifetroban arm, 50% of the initial reactions occurred at 60-mg and the other half at 100-mg. One subject on placebo experienced a provoking dose reaction at 60 mg on Day 2 and another AIR on Day 3 at 100 mg. The severity of the 2 AIRs were comparable to one another. All other subjects experienced a single AIR during the aspirin desensitization process. Further information concerning AERD Phase 2a AIRs by aspirin dose is presented in Table 6 below.

TABLE 6

Incidence of an AIR by Aspirin Dose

| No. of Subjects (%)* Aspirin Dose (mg) | Ifetroban n = 10 | Placebo n = 3** | All AIR Subjects N = 13 |
|---|---|---|---|
| 30 | 0 | 0 | 0 |
| 60 | 5 (50) | 3 (100) | 8 (62) |
| 100 | 5 (50) | 1 (25) | 6 (46) |
| 150 | 0 | 0 | 0 |
| 325 | 0 | 0 | 0 |

*Based on AIR population only; **1 subject experienced 1 AIR at 60 mg and 1 AIR at 100 mg hence counted twice. AIR = Aspirin-induced Reaction The incidence of the AIR provoked at each aspirin dose was evaluated between treatment groups and summarized in Table 6. All subjects who experienced an AIR reacted to a provoking dose of 60 and/or 100 mg. No reaction occurred after the 100-mg provoking dose. All initial reactions in the placebo arm occurred at the 60-mg dose while in the ifetroban arm, 50% of the initial reactions occurred at 60-mg and the other half at 100-mg. One subject on placebo experienced a provoking dose reaction at 60 mg on Day 2 and another AIR on Day 3 at 100 mg. The severity of the 2 AIRs were comparable to one another. All other subjects experienced a single AIR during the aspirin desensitization process.

The severity of the AIRs were compared between treatment groups by the number of separate symptoms that manifested during the aspirin challenge. The total number of symptoms are based on 14 AIRs that occurred in 13 subjects, 10 ifetroban-treated subjects and 3 placebo-treated subjects. As mentioned previously, 1 subject on the placebo arm experienced 2 AIRs. The average number of symptoms per AIR was comparable between treatment groups. Both arms experienced a bronchial reaction (<20% decrease in FEV1, wheezing, chest tightness) as part of the AIR at a similar rate. While an upper respiratory effect (rhinorrhea, nasal obstruction, sneezing) was equally as common between treatment groups, an ocular manifestation seems to trend toward the placebo arm more often than on the ifetroban arm. AIR severity in the study is reported in Table 7 below.

TABLE 7

Severity of an AIR by Clinical Manifestation

| Category/Feature | Ifetroban n = 10 | Placebo n = 3 | All AIR Subjects N = 13 |
|---|---|---|---|
| All Symptoms* | 43 | 20 | 63 |
| Mean(SD) | 4.3(1.34) | 5.00(0.82) | 4.50(1.22) |
| Median | 4 | 5 | 4 |
| Min, Max | 3.7 | 4.6 | 3.7 |
| <20% decrease in FEV1 | 9 | 4 | 13 |
| Mean | 0.9 | 1 | 1 |
| Upper Respiratory | 25 | 11 | 36 |
| Mean | 2.5 | 2.8 | 2.6 |
| Lower Respiratory | 13 | 5 | 18 |
| Mean | 1.3 | 1.3 | 1.3 |
| Ocular | 5 | 4 | 9 |
| Mean | 0.5 | 1 | 0.6 |

In conclusion, in this clinical study, ifetroban at 200 mg/day was shown to be well tolerated and safe in subjects with a history of AERD. There was no increase in AEs reported in the ifetroban group compared to placebo. All subjects completed treatment and aspirin desensitization. The primary endpoint was met; ifetroban did not cause a ≥20% decrease in FEV1. The results of this small safety study demonstrated that ifetroban was safe when administered to patients with AERD. In addition, results from the study suggest the symptoms of aspirin desensitization in AERD patients may be diminished by the use of ifetroban at a dose of 200 mg/day.

The primary endpoint was not met; ifetroban did not cause a ≥20% decrease in FEV1 during the course of IMP treatment or the aspirin desensitization process. Mean changes from baseline FEV1 remained well below 20% throughout the treatment period in both groups with no clear trends observed. While no appreciable difference was observed in the proportion of subjects with worsening NIFR or TNSS between treatment groups, there is an observed trend in favor of the ifetroban group toward greater improvements to NIFR and TNSS during phase A and phase B. Moreover, there is an apparent trend toward fewer rescue medications in favor of the ifetroban group and, while an upper respiratory effect was equally as common between treatment groups, an ocular manifestation seems to trend toward the placebo arm more often than on the ifetroban arm. Although the sample size is not sufficient to demonstrate statistically significant treatment efficacy, these data are encouraging. Larger studies with longer treatment duration are needed to make formal conclusions about ifetroban efficacy in AERD. The results of this small safety study support further investigations of ifetroban at a therapeutic dose of 200 mg/day for subjects with AERD.

CONCLUSION

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

REFERENCES

Armour C L, Johnson P R, Alfredson M L, Black J L. Characterization of contractile prostanoid receptors on human airway smooth muscle. Eur J Pharmacol 1989 Jun. 20; 165(2-3):215-22.

Bochenek G, Nagraba K, Nizankowska E, Szczeklik A. A controlled study of 9alpha,11beta-PGF2 (a prostaglandin D2 metabolite) in plasma and urine of patients with bronchial asthma and healthy controls after aspirin challenge. J Allergy Clin Immunol 2003 April; 111(4):743-9.

Fischer A R, Rosenberg M A, Lilly C M, Callery J C, Rubin P, Cohn J, et al. Direct evidence for a role of the mast cell in the nasal response to aspirin in aspirin-sensitive asthma. J Allergy Clin Immunol 1994 December; 94(6 Pt 1):1046-56.

Laidlaw T M, Kidder M S, Bhattacharyya N, Xing W, Shen S, Milne G L, et al. Cysteinyl leukotriene overproduction in aspirin-exacerbated respiratory disease is driven by platelet-adherent leukocytes. Blood 2012 Apr. 19;119 (16):3790-8.

Liu T, Laidlaw T M, Feng C, Xing W, Shen S, Milne G L, et al. Prostaglandin E2 deficiency uncovers a dominant role for thromboxane A2 in house dust mite-induced allergic pulmonary inflammation. Proc Natl Acad Sci USA 2012 Jul. 31; 109(31):12692-7.

Liu T, Laidlaw T M, Katz H R, Boyce J A. Prostaglandin E2 deficiency causes a phenotype of aspirin sensitivity that depends on platelets and cysteinyl leukotrienes. Proc Natl Acad Sci U S A 2013 Oct. 15; 110(42):16987-92.

Murakami M, Naraba H, Tanioka T, Semmyo N, Nakatani Y, Kojima F, et al. Regulation of prostaglandin E2 biosynthesis by inducible membrane-associated prostaglandin E2 synthase that acts in concert with cyclooxygenase-2. J Biol Chem 2000 Oct. 20; 275(42):32783-92.

Ogletree M L, Allen G T. Interspecies differences in thromboxane receptors: studies with thromboxane receptor antagonists in rat and guinea pig smooth muscles. J Pharmacol Exp Ther. 1992 February; 260(2):789-94.

Pettipher R, Hansel T T, Armer R. Antagonism of the prostaglandin D2 receptors DP1 and CRTH2 as an approach to treat allergic diseases. Nat Rev Drug Discov 2007 April; 6(4):313-25.

Picado C, Fernandez-Morata J C, Juan M, Roca-Ferrer J, Fuentes M, Xaubet A, et al. Cyclooxygenase-2 mRNA is downexpressed in nasal polyps from aspirin-sensitive asthmatics. Am J Respir Crit Care Med 1999 July; 160 (1):291-6.

Sladek K, Dworski R, Soja J, Sheller J R, Nizankowska E, Oates J A, et al. Eicosanoids in bronchoalveolar lavage fluid of aspirin-intolerant patients with asthma after aspirin challenge. Am J Respir Crit Care Med 1994 April; 149(4 Pt 1):940-6.

Sousa A, Pfister R, Christie P E, Lane S J, Nasser S M, Schmitz-Schumann M, et al Enhanced expression of cyclo-oxygenase isoenzyme 2 (COX-2) in asthmatic airways and its cellular distribution in aspirin-sensitive asthma. Thorax 1997 November; 52(11):940-5.

Szczeklik A, Sladek K, Dworski R, Nizankowska E, Soja J, Sheller J, et al. Bronchial aspirin challenge causes specific eicosanoid response in aspirin-sensitive asthmatics. Am J Respir Crit Care Med 1996 December; 154(6 Pt 1):1608-14.

Yoshimura T, Yoshikawa M, Otori N, Haruna S, Moriyama H. Correlation between the prostaglandin D(2)/E(2) ratio in nasal polyps and the recalcitrant pathophysiology of chronic rhinosinusitis associated with bronchial asthma. Allergol Int 2008 December; 57(4):429-36.

What is claimed is:

1. A method of reducing a rescue medication needed as a result of an aspirin-induced reaction in a human patient suffering from aspirin exacerbated respiratory disease (AERD), comprising:
    administering ifetroban or a pharmaceutically acceptable salt thereof to the patient in a daily dose of 200 mg, wherein the ifetroban or a pharmaceutically acceptable salt thereof is administered orally; and
    subsequently administering aspirin to the human patient suffering from AERD.

2. The method of claim 1, wherein the ifetroban is ifetroban sodium.

3. The method of claim 1, wherein the ifetroban or a pharmaceutically acceptable salt thereof is formulated in a pharmaceutically acceptable solid oral dosage form.

4. The method of claim 3, wherein the pharmaceutically acceptable oral dosage form is a capsule or tablet.

* * * * *